United States Patent [19]
Weedle

[11] 3,931,819
[45] Jan. 13, 1976

[54] DRAINAGE BAG FOR HUMAN BODY

[75] Inventor: Rosemary B. Weedle, Grafton, Va.

[73] Assignees: Phillip M. Weddle, Grafton; Auzville Jackson, Jr., Richmond, both of Va.; a part interest to each

[22] Filed: Jan. 30, 1975

[21] Appl. No.: 545,352

Related U.S. Application Data
[63] Continuation of Ser. No. 398,382, Sept. 18, 1973, abandoned.

[52] U.S. Cl. .............................................. 128/283
[51] Int. Cl.² .......................................... A61F 5/44
[58] Field of Search .................................. 128/283

[56] References Cited
UNITED STATES PATENTS

| | | | |
|---|---|---|---|
| 2,595,934 | 5/1952 | Ginsburg | 128/283 |
| 2,684,676 | 7/1954 | Perry | 128/283 |
| 2,788,785 | 4/1957 | Present | 128/283 |
| 3,421,505 | 1/1969 | Freeman | 128/283 |

Primary Examiner—Richard A. Gaudet
Assistant Examiner—Henry S. Layton
Attorney, Agent, or Firm—Auzville Jackson, Jr.

[57] ABSTRACT

The disclosure is directed to a drainage bag for the human body especially usable for patients who have undergone a colostomy, ileostomy, urostomy or the like. The bag has a cloth backing, a special contour to fit the body and enable it to be supported by standard type of underwear having elastic leg bands, and an unobstructed reclosable opening for easy draining.

10 Claims, 11 Drawing Figures

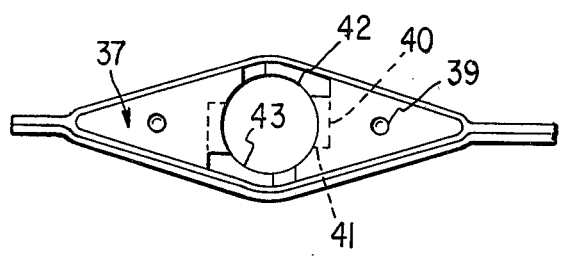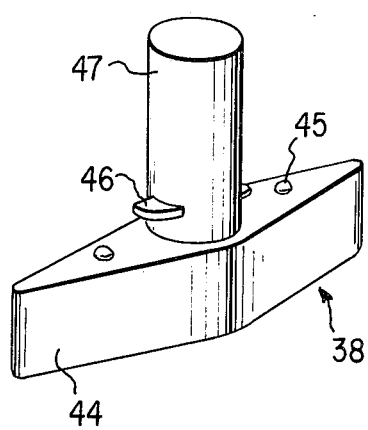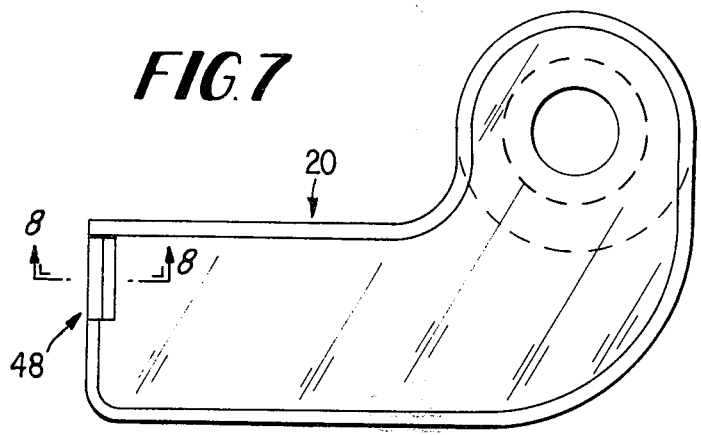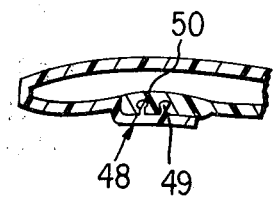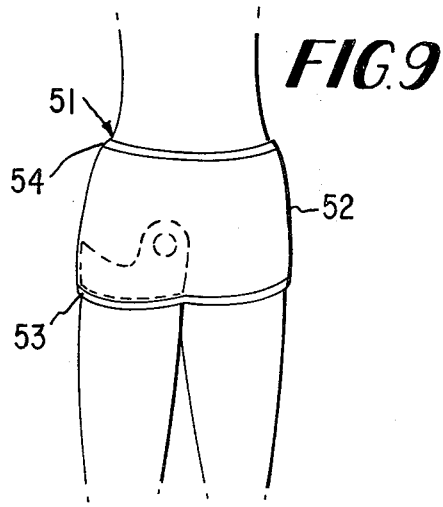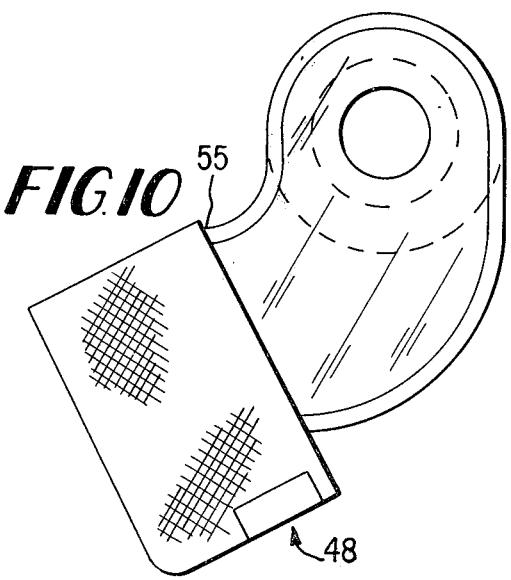

DRAINAGE BAG FOR HUMAN BODY

This is a continuation of application Ser. No. 398,382, filed Sept. 18, 1973 and now abandoned.

BACKGROUND OF THE INVENTION

The present invention relates to an improved drainage bag for the human body of the type referred to as urostomy drainage bags, ileostomy drainage bags, colostomy drainage bags, and the like. The bag is designed to enhance the comfort of its wearer, to permit the use of the bag for greater periods of time, to permit the bags to be more easily worn and more flexible in their use, and to permit their use in a more convenient manner.

A drainage bag for the human body is necessary for persons who have undergone surgery such as a colostomy, ileostomy, urostomy or the like. Such surgical procedures often involve the diversion of the intestines or other parts of the human body through the person's abdominal wall to form a stoma which permits the discharge and drainage from the human body of waste products such as fecal matter or urine. This drainage through the stoma is with little or no control by the person having the operation and it is necessary to provide a container such as a drainage bag affixed to the body over the stoma to receive such drainage.

Presently the most widely used bags are of a disposable plastic nature which hang down from the front of the body and are removed and thrown away as such becomes necessary. The bag adjacent the skin of the body is of a plastic and impermeable nature which is uncomfortable to wear when hot and frequently is irritating to the skin. Usually this type of bag is supported at the top which lacks convenience and comfort and the bag usually lays in a manner that is to the front, making it uncomfortable and protrudes in an objectional manner during normal usage.

SUMMARY OF THE INVENTION

In accordance with the present invention, the drainage bag is made from an impermeable plastic heat sealed around its periphery with a cloth backing laminated to that surface of the bag which is to lie adjacent the skin. This cloth backing extends over the full surface of the bag except for the portion surrounding the opening which fits over the stoma. This enables a mounting pad to be sealed by a liquid tight seal directly to the impermeable plastic layer forming the body side of the bag without the intermediary cloth backing.

The bag has a specially curved design that fits the contour of the body to extend outward and partly around the side of the body with the bottom portion and contents being supported in a major way by the elastic leg band of a standard type of underwear. The drain opening is unobstructed for easy draining when opened and is reclosable by either a removable plug or an integral plastic zipper opening located near the top portion of the bag.

An adhesive disc affixes the bag to the surface of the human body surrounding the stoma and is adapted to be reusable by utilization of a double-sided adhesive disc removably applied to the mounting pad of the bag.

The bag provides a maximum of security for all normal activities as well as during sleep and is more desirable during wear and social activities, including sexual intercourse, since the design goes to the side rather than the front part of the body.

Because of the nature of the opening of the drainage bags fewer accidents will occur due to leakage, and a longer time period permitted before the emptying of the bag.

Many other advantages and a better understanding of the nature of the bag of the present invention will become apparent from the following description taken in connection with the accompanying drawings.

BRIEF DESCRIPTION OF THE DRAWINGS

FIG. 5 is a partial bottom view of the drainage opening of FIG. 4 with the plug removed.

FIG. 6 is a perspective view of the drainage plug after it has been removed.

FIG. 7 is a second embodiment of the invention especially adapted tas a ileostomy or colostomy bag.

FIG. 8 is a partial sectional view taken on Section 8—8 of FIG. 7 and showing the integral locking zipper for closing the opening thereof.

FIG. 9 shows the bag of the invention being worn under a standard type of undergarment having an elastic leg band which supports the bottom of the bag and causes it to lay adjacent the body in the front and as it curves around to the side.

FIG. 10 is a view of the bag of FIG. 7 and showing the foot portion folded over onto itself in a manner to permit drainage of the bag while it is still in place.

DESCRIPTION OF THE INVENTION

Figure 1:
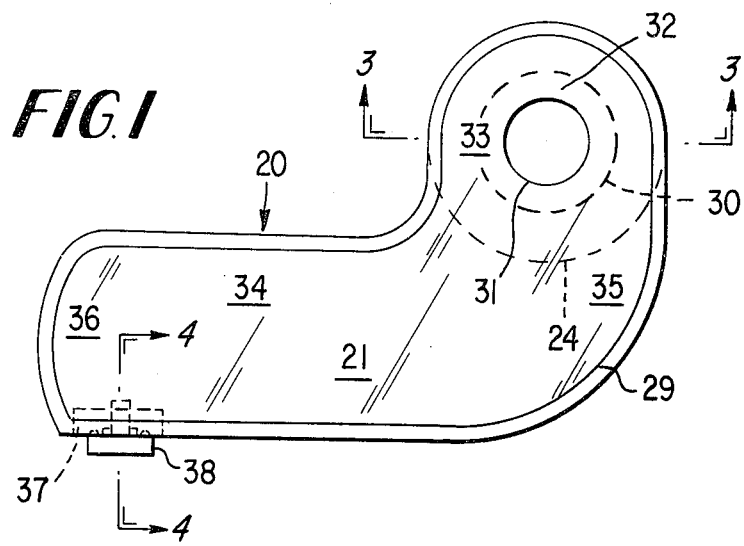
FIG. 1 is a front view of a drainage bag of this invention especially adapted as a urostomy drainage bag or pouch.
Figure 2:
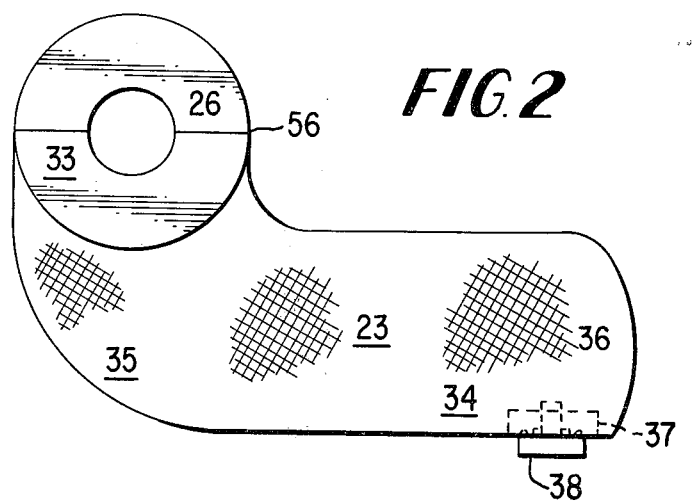
FIG. 2 is a back view of the drainage bag of FIG. 1.
Figure 3:
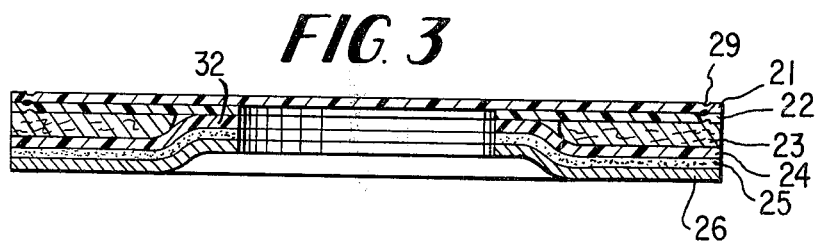
FIG. 3 is a transverse sectional view taken on Section 3—3 of FIG. 1 (thicknesses are exaggerated and not to scale).

With reference to FIGS. 1, 2 and 3, there is shown a drainage bag especially adaptable for use as a urostomy drainage bag. It has a front plastic layer 21 preferably made of transparent polyethylene which is of a flexible impermeable nature and which may be readily sealed to another layer of it or similar material. The drainage bag 20 also has a back plastic layer 22 which peripherally is cut to the same dimensions of the front plastic layer and is made of the same plastic material such as polyethylene or at least a material having the same characteristics and which is readily sealable to the front plastic layer. It is not essential that this layer be transparent as is required of the front layer. Laminated to the entire back plastic layer 22 and having the same peripheral dimensions is a soft layer 23 preferably made of a soft flannel cloth but which may be of any soft material such as a soft porous synthetic fiber paper or a soft non-woven cloth and so forth. It must be of a sanitary material which is laminatible to the back plastic layer 22 and which is comfortable when adjacent the skin of the wearer so as not to cause heat buildup or irritation to the skin to the extent an impermeable plastic layer would cause.

A circular sealing washer 24 made of a flexible impermeable plastic material and sealable preferably by heat to the back plastic layer is provided at the rear of the drainage bag and has adjacent thereto an adhesive layer 25 which is of a material which will cause the bag to adhere to the surface skin of its wearer in a non-irritating manner and prevent the seepage of the drainage from the human body from attacking it but instead directing such drainage into the bag for handling, shipping, storage and the like. The adhesive layer is protected until use by a peel-off paper 26 having a cut line 56 permitting a portion of the peel-off paper to be removed before the remainder is moved for the easily handling prior to placing the adhesive layer around the stoma and onto the surface skin.

Figure 11:
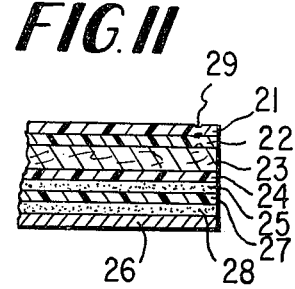
FIG. 11 is a variation of the view of FIG. 3 showing the use of a throw away adhesive disc having adhesive on both sides to permit reuse of the drainage bag.

In FIG. 11 there is shown a preferred modification of the first embodiment as shown in FIG. 3. Rather than having the sealing washer with an adhesive layer and a peel-off paper, an adhesive carrier layer made of a plastic disc 27 which has a first adhesive layer 25 for mounting to the sealing washer 24 and a second adhesive layer 28 for mounting and being compatible with the skin of the wearer is provided. This disc is a disposable item and would have a peel-off paper 26 on one side and a second peel-off paper (not shown) similar to peel-off paper 26 on the other side.

When the drainage bag 20 is to be readied for use, it is first cleaned and dried, if necessary, and especially in the exposed surface of the sealing washer 24. Then the plastic disc has its peel-off paper protective layers removed and one adhesive layer applied to the sealing washer and the other adhesive layer applied to the skin of the wearer in the vicinity surrounding the stoma. The front plastic layer 25 must be transparent in the vicinity of the opening in the back plastic layer 31 so that the stoma can be viewed through this transparent window when the bag is being positioned in place. If desired, the remainder of the front plastic layer 21 may be opaque by some form of treatment or otherwise as long as the transparent window is provided. The adhesive layers must be provided on the plastic disc 27 so they will at all times adhere preferentially to the plastic disc so that once the bag is used and is desired to be reused the plastic disc can be peeled off of the sealing washer 24 bringing with it most, if not all, of the adhesive layer so as to eliminate the necessity of cleaning much, if any, adhesive off of the sealing washer.

As seen in FIG. 1, the front plastic layer 21 is adhered to the back plastic layer 22 about its entire periphery by its peripheral seal 29. This is preferably a heat seal of the type widely practiced in sealing the edges of two plastic sheets of polyethylene or similar plastics together. This peripheral seal extends and bridges over the drain 37 which will be more fully described hereinafter.

While it was stated earlier that the soft layer 23 was laminated over the entire surface of the back plastic layer 22, this is not always truly correct since there is an annular area surrounding the opening in the back plastic layer 31 which is not laminated because the soft layer 23 has a larger opening 30 which surrounds this opening 31. The annular area between opening 31 and the larger opening 32 gives an exposed region to the back plastic layer 22 permitting to be sealed directly in an impermeable fashion to the sealing washer 24 which has an opening similar in size to the back plastic layer 31. This is important because if the soft layer extended into this region a liquid tight seal could not be provided as conveniently and could not be provided at all without special treatment such as impregnation of the soft layer with a relatively thick layer of adhesive or special choice of material such as a thermoplastic soft layer which is sealed by a thermal melting or fusion thereof.

Preferably the sealing washer 24 is adhered to the back plastic layer 21 in this annular region to provide a seal 32 as best seen in FIGS. 1, 3 and 11. Of course, if the soft layer 23 is made of a material having a thermoplastic nature the three can be heat sealed together in one operation which would cause a fusion of the soft layer in the vicinity of the sealing so as to provide a liquid tight fusion zone and an annular seal between the sealing washer 24 and the back plastic layer 22. While this would limit the choice of materials for the soft layer, it has the advantage that the back plastic layer and the soft layer can be laminated in roll form on high production machinery prior to being cut and assembled into a drainage bag.

Until now little has been said about a most important aspect of the invention which is the special shape of the drainage bag as is best seen in FIGS. 1 and 9. The drainage bag is shaped like an ankle-foot with the ankle portion 33 being of a width approximately the size of the circular sealing washer and extending vertically from the main body of the drainage bag so as to be the portion which surrounds the stoma to accept the drainage therefrom. The foot portion 34 is divided into a heel portion 35 and a toe portion 36. The heel portion directly beneath the ankle portion 33 receives the drainage which accumulates along the bottom of the foot portion 34 which is prevented from escaping through the reclosable drain 37 located in the toe portion at its bottom by drain plug 38. Thus, the drainage from the stoma collects in the bottom and toe portion of the foot portion of the drainage bag.

The foot portion extends outwardly and to the side of its wearer as seen in FIG. 9, where there is shown a human torso 51 wearing a standard type of elastic underwear or underpants 52 which are readily available and commonly worn by people who have no post-surgical problems. The undershorts or underpants have elastic leg bands 53 or a tight fitting band thereabout and an elastic waistband 51. Such shorts are usually made of a knitted material with some degree of stretchability of the cloth from which it is made.

When the bag is mounted on the human body as shown in FIG. 9, it hangs a distance downward so that the bottom of the foot portion of the bag rests on the tight fitting elastic leg band with a toe portion extended outwardly and to the side closely adjacent to the human skin to be held in place by the cloth of the undershorts with the majority of the weight being supported by the elastic band 53 so that little or no weight of the drainage is placed on the ankle portion of the drainage bag to pull on the adhesive layer holding the bag to the skin of the body. Thus all the adhesive layer is required to do is to hold the bag close to the body with little or no need to support the weight of the drainage. Also the bag is closely fitting to the body with the soft layer adjacent the skin making it more comfortable and less irritating especially in hot weather than would be the case of the bags principally used at the time of this invention. Still further, the bag is held in a manner that is relatively safe from embarrassment and permits greater activity, both physically and socially, by its wearer.

Figure 4:
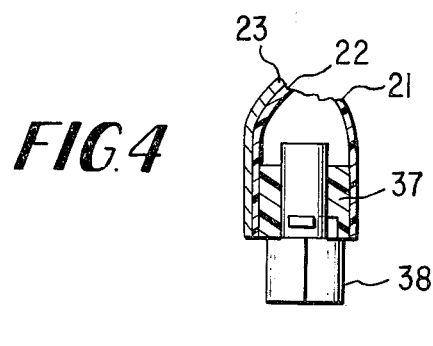
FIG. 4 is a partial sectional view taken on Section 4—4 of FIG. 1 and showing the assembled drainage plug.

The drain 37 located in the toe portion of the embodiments of FIG. 1 and as best seen in FIGS. 4, 5 and 6 has two drain locking dimple recesses 39 to drain undercuts 40 having two drain undercut stop portions 41, and two drain undercut entrance portions 42 all for receiving the bayonet locking arrangement of the drain plug 38. The drain has an opening 43 which in normal use is stoppered by drain plug stopper portion 47 which closely mates therein.

The drain plug 38 has a turning handle 44 and two drain plug locking dimples 45 and two drain plug bayonet lugs 46. It is to be noted from FIGS. 4 and 5 that the drain 37 is of a relatively flat nature and preferably made from an easily moldable thermoplastic such as polyethylene which lends itself to being readily sealed between the front plastic layer 21 and the back plastic layer 22 preferably by a thermal seal. The flat nature of the drain permits being readily sealing to the bag and is more comfortable to the wearer and lies closer to the body with less of a protrusion through the clothes or to catch on some obstruction.

The drain plug is also shaped in a mating fashion having a complimentary relatively flat handle which is used to first insert the drain plug 47 into the opening 43 with the bayonet lugs 46 entering into the entrance portion of the undercut 42. This is done with the flat portion of the plug at a 90° angle to the flat portion of the drain. When the bayonet lugs in the stopper portion are received fully into the drain the handle is rotated in a clockwise direction, when viewed looking into the opening 43, with the bayonet lugs entering into the undercut until the rotation of the drain plug 38 is stopped by the bayonet lugs contacting stop portions 41. Just prior to the stopping of the rotation the drain plug locking dimples 45 ride up on the body of the drain 37 and then drop into the drain locking dimple recesses 39 when the drain plugs turning is stopped. In order for the recesses and dimples to mate there requires a slight flexing of the parts to overcome the fact that the drain undercuts and bayonet lugs cause the plug to be inserted fully into the drain until the handle of the plug is stopped by the main body of the drain. Thus, the dimples and recesses until they mate with one another, cause the plane between the handle and the bottom of the drain to be forced out of line and provide a flexing of the parts until the turning is complete. This increases the resistance to the rotation of the plug and prevents it being accidentally rotated out of its alignment with the drain during normal wear.

When it is desired to empty the bag while still on the wearer, the underpants are lowered and the bag brought around so that the drain overlies a receptacle into which it is to be drained. The plug is rotated now in a counter-clockwise direction, first against the resistance of the dimples riding out of the recesses causing a flexing of the parts, and when the plug is rotated 90° the bayonet lugs leave the undercuts in the vicinity of the undercut entrance portions where they are no longer held by the undercuts tightly against the drain. At that time the plug including the stopper portion can be withdrawn permitting the contents of the bag to be drained into a receptacle and the end wiped off or cleaned as necessary prior to reinserting the plug, placing the bag back into position and raising the shorts to hold it in such position for continued use. None of the above operations requiring that the bag adhesive layer be removed from the skin.

The above description was made in connection with the embodiments shown in FIG. 1 which is primarily for a urostomy bag where the liquid is highly fluid with no solid content. However, in the case of an ileostomy or colostomy bag a different opening which is recloseable in the toe is provided such as shown in FIGS. 7, 8 and 10. Here an integral zipper 48 having integral ridges 49 mating in a friction fit with integral zipper valleys 50 are provided. Generally, these zippers are made up in a separate flat manner to be heat sealed into the body of the bag but they may be integrally molded with the bag as an alternative. At any rate, each layer has complementary ridges and valleys with the ridges having a greater width at their outermost portion than at their base portion which mate as shown in FIG. 8 with the valleys so that the knob or wider width of the outer portion of the ridge causes a stretching apart of the valleys until they accommodate at the base of the bag to provide a type of integral plastic zipper that is generally known in the art as plastic bags for storing items in the kitchen and so forth.

It is to be noted that the recloseable drain opening is at the top portion of the toe and not at the bottom portion as shown in the first embodiment. This is so that in normal usage the less fluid drainage resulting from an ileostomy or colostomy will collect at the bottom of the bag without any danger of it draining through an imperfect seal. It is necessary in these bags to provide a larger opening which is the reason for the different seal to prevent it from plugging up during drainage. When it is desired to drain this bag, the undershorts are lowered and the bag folded on top of itself generally in the vicinity of fold line 55 as best shown in FIG. 10 to a downward position overlying a suitable receptacle. The position shown in FIG. 10 plus a simultaneous bending of the body causes the drain to be located below the normal bottom portion of the bag and, at the lowermost regions of the bag for ready emptying. The integral plastic zipper is opened and the contents of the drain bag worked out and emptied into the receptacle. To the extent necessary the bag is washed, rezippered and placed back in its normal position as shown in FIG. 9 without the necessity of removing the bag and its adhesive layer from the body.

Generally, when it is necessary to completely remove the bag from the body of its wearer, it is carefully removed from the vicinity of the stoma and carefully cleaned and set aside to dry for reuse especially when using the plastic disc with double side adhesive layers as shown in FIG. 11.

The bag permits a number of reuses. Because of its layer adjacent to human skin and the special shape bringing the bag drainage first downward and then the main body of the receptacle outward around the side of the human body to have its weight supported by standard type of elastic or tight fitting leg band undershorts, it is vastly more comfortable and convenient to use and to wear than the bags presently available.

When it is desired to place the bag in position, the peel-off paper is removed from the adhesive layers and in the case of a double sided adhesive carrying plastic disc, the side to be applied to the sealing washer is first so applied, then the remaining side carefully located through the transparent window of the front plastic layer over the stoma and around its edges and caused to adhere into place with the heel portion of the drainage bag directly below the stoma and with the bottom and toe portion extending outwardly to the side of the body in a manner that the bottom portion rests on the tight fitting or elastic leg bands of the undershorts which support the weight of any material drained into the bag with the body of the undershorts holding the drainage bag flat against the front and side of the body.

The bag is drained as necessary until it becomes time to again remove the bag and clean it and dry it.

While the invention has been specifically described above, it will be appreciated that the invention may be embodied in numerous other forms without departing from the spirit or central characteristics of the invention herein. The present embodiments are therefore to be considered in all respects as illustrative and not restrictive, the scope of the invention being indicated by the appended claims. rather than by the foregoing description and all changes which come within the meaning and range of the equivalency of the claims are therefore intended to be embraced therein.

What is claimed is:

1. A drainage bag for attaching around a drainage opening in the human body and to be worn adjacent the skin comprising:
    a soft layer of the peripheral dimensions of the drainage bag and having an opening therein,
    a back plastic layer of the peripheral dimensions of the drainage bag and having an opening therein affixed to said soft layer to be coextensive therewith and having its opening coaxial with said soft layer opening,
    a front plastic layer of the peripheral dimensions of the drainage bag and sealed about its periphery to said back plastic layer on the side of said back plastic layer not laminated to said soft layer,
    a sealing washer on the back side of said drainage bag having an opening therein, and
    a seal between the area surrounding said seal washer opening and the area surrounding said back plastic layer opening.

2. The drainage bag of claim 1 wherein said sealing washer has an adhesive layer means applied thereto for affixing said bag to the human body and wherein said adhesive layer means is protected until use by a peel-off layer which may be readily peeled from the adhesive layer means without any substantial amount of adhesive coming with it.

3. The drainage bag of claim 2 wherein said adhesive layer means includes an adhesive carrier layer which has a layer of adhesive on each side thereof with one layer of adhesive mounted to said sealing washer and the other adhesive layer adapted for adhering to the skin.

4. The drainage bag of claim 1 wherein said bag has a foot and ankle shape with the ankle area containing the opening to fit over a stoma and a foot portion containing the drainage holding area, a heel portion, a bottom portion and a toe portion, located in said foot portion, with said heel portion located substantially directly below said ankle portion and said bottom portion and toe portion extending in a direction that when the drainage bag is worn, they extend to the side of the wearer and away from the center of the wearer's torso with the bottom portion being supportable by a tight leg band of common underpants, and a recloseable opening located in said toe portion for periodic draining of said bag for reuse without removing said bag from the wearer.

5. The drainage bag of claim 4 wherein said recloseable opening is located at the bottom of said toe portion and includes a flat female unobstructed drain sealed to said bag and a removable male plug for stoppering said drain.

6. The drainage bag of claim 5 wherein said removable male plug has a flat turning handle portion, bayonet lugs and locking dimples and said female drain has complementary bayonet lug receiving means and dimple receiving recesses whereby said plug may be inserted into said drain and rotated and locked in place.

7. The drainage bag of claim 4 wherein said recloseable opening is located at the top of said toe portion whereby no leaking will occur in normal use in event of an imperfect seal of said opening and whereby said bag may be emptied of its contents without being removed from the wearer by folding down along a diagonal fold so the opening is in a lowered position below the normal position of said bottom portion of said bag.

8. The drainage bag of claim 7 wherein said recloseable opening is sealed by a plastic zipper.

9. The drainage bag of claim 4 wherein said sealing washer has an adhesive layer means applied thereto for affixing said bag to the human body and wherein said adhesive layer means is protected until use by a peel-off layer which may be readily peeled from the adhesive layer means without any substantial amount of adhesive coming with it.

10. The drainage bag of claim 9 wherein said adhesive layer means includes an adhesive carrier layer which has a layer of adhesive on each side thereof with one layer of adhesive adhering to said sealing washer and the other adhesive layer adapted for adhering to the skin.

* * * * *